United States Patent [19]

Deckner et al.

[11] Patent Number: 4,919,934
[45] Date of Patent: Apr. 24, 1990

[54] COSMETIC STICKS

[75] Inventors: George E. Deckner, Trumbull; Rupali A. Kulkarni, Huntington, both of Conn.

[73] Assignee: Richardson-Vicks Inc., Shelton, Conn.

[21] Appl. No.: 317,773

[22] Filed: Mar. 2, 1989

[51] Int. Cl.$^5$ .......................... A61K 7/00; A61K 7/32; A61K 7/42; A61K 7/44
[52] U.S. Cl. ........................... 424/401; 424/59; 424/60; 424/65; 424/66; 424/67; 424/68; 424/64; 514/772; 514/787; 514/789; 514/817; 514/844; 514/873; 514/887; 514/919; 514/953; 514/969
[58] Field of Search ............... 424/401, 59, 60, 65, 424/66, 67, 68, 64; 514/772, 787, 789, 817, 844, 873, 887, 919, 953, 969

[56] References Cited

U.S. PATENT DOCUMENTS

| | | | |
|---|---|---|---|
| 3,793,446 | 2/1974 | Moeller et al. | 424/48 |
| 3,793,463 | 2/1974 | Moeller et al. | 424/300 |
| 3,830,930 | 8/1974 | Moeller et al. | 424/308 |
| 4,265,663 | 5/1981 | Gillicinks et al. | 106/10 |
| 4,343,863 | 8/1982 | Lawrence et al. | 428/485 |
| 4,466,909 | 8/1984 | Stayner | 252/49.5 |
| 4,664,820 | 5/1987 | Magavran et al. | 252/28 |
| 4,702,916 | 10/1987 | Geria | 424/400 |
| 4,797,219 | 1/1989 | Guttierrel et al. | 252/56 |
| 4,859,352 | 8/1989 | Waynick | 252/41 |

*Primary Examiner*—Shep K. Rose
*Attorney, Agent, or Firm*—David K. Dabbiere; Douglas C. Mohl; Jack D. Schaeffer

[57] ABSTRACT

Disclosed are wax based cosmetic stick compositions comprising: from about 10% to about 50% of a wax type solidifying agent; and from about 5% to about 90% of a polyalphaolefin. These compositions preferably comprise from about 1.0% to about 40% of an active component, such as a sunscreen agent, analgesic, moisturizing and antiperspirant or a deodorant active.

10 Claims, No Drawings

COSMETIC STICKS

BACKGROUND OF THE INVENTION

The present invention relates to cosmetic compositions in the form of solid sticks such as sun care, moisturizing or analgesic sticks and antiperspirant/ deodorant sticks. These compositions have excellent efficacy as well as improved cosmetics.

There are three main types of such cosmetic formulations: compressed powder sticks, gel sticks, and wax sticks. While each of these formulation types may have advantages in certain use situations, each also has disadvantages. For example, compressed powder sticks are often brittle and hard, and leave a cosmetically-unacceptable dust upon application. Gels, while offering very good aesthetic characteristics, may be unstable due to interaction between the soap gelling agents typically used to solidify such sticks and the stick's "active" material (e.g., sunscreens and antiperspirant salts). Wax-based formulations can also yield cosmetically-unacceptable products due to such facts as hardness, greasiness, and stickiness.

Cosmetic sticks preferably glide easily over the skin surface, are not perceived as feeling gritty, and do not leave a visible residue. Soaps/alcohol gels can provide some of such cosmetic benefits. Examples of such soap gels are disclosed in U.S. Pat. No. 2,732,327, to Teller, issued Jan. 24, 1956; U.S. Pat. No. 2,857,315, to Teller, issued Oct. 21, 1958; U.S. Pat. No. 2,900,306, to Slater, issued Aug. 18, 1959; and U.S. Pat. No. 2,970,083, to Bell, issued Jan. 31, 1961. In addition, U.S. Pat. No. 4,382,742, to Marschner, issued Apr. 3, 1984 describes aqueous, transparent sticks containing bicarbonate in a propylene glycol/metal stearate gel. Wax based bicarbonate sticks containing silicones are described in U.S. Pat. No. 4,126,679, to Davy et al., issued Nov. 21, 1978. Emulsion sticks are also well known, having been disclosed, for example, in U.S. Pat. 4,122,029, to Gee et al., issued Oct. 24, 1978, and U.S. Pat. No. 4,265,878, to Keil, issued May 5, 1981.

While cosmetic sticks are old as evidenced by certain of the above patents, none of these publications suggests the criticality of the specific combination of components described by the present invention. This combination of components gives cosmetic sticks which are both highly efficacious and cosmetically pleasing.

It is therefore an object of the present invention to provide cosmetic sticks which have excellent cosmetic properties (e.g. ease of application to skin, "glide", and lack of visible residue) and are easy to manufacture. A further object of the present invention is to provide cosmetic sticks which very effectively deliver active materials to the skin, particularly sunscreen, analgesic, moisturizing, antiperspirant and deodorant actives. A still further object of the present invention is to provide cosmetic sticks with good high temperature stability. A still further object is to provide cosmetic sticks which impart a non-tacky, non-greasy cosmetically elegant feel to the skin.

SUMMARY OF THE INVENTION

The present invention relates to wax based cosmetic stick compositions comprising:
(a) from about 10% to about 50% of a wax type solidifying agent; and
(b) from about 5% to about 90% of a polyalphaolefin.

These compositions preferably comprise from about 1.0% to about 40% of an active component, such as a sunscreen agent, analgesic, moisturizing and antiperspirant or a deodorant active.

All percentages and ratios used herein are by weight of the total composition and all measurements made at 25° C., unless otherwise designated.

DETAILED DESCRIPTION OF THE INVENTION

Wax Type Solidifying Agent

An essential component of the compositions herein is at least one wax type solidifying agent. Among such wax type solidifying agents useful herein are the high melting point waxes having a melting point of from about 65° C. to about 102° C., low melting point waxes having a melting point of from about 37° C. to about 65° C., and preferably mixtures thereof.

High melting point waxes include beeswax, spermaceti, carnauba, baysberry, candelilla, montan, ozokerite, ceresin, paraffin, hydrogenated castor oil (castor wax), synthetic waxes such as Fisher-Tropsch waxes, microcrystalline waxes, ethylene glycol diesters, triglyceride (preferably $C_{18}$–$C_{36}$) waxes and ethylene/vinyl acetate copolymers, and mixtures thereof. Ozokerite wax is a preferred high-melting point wax useful herein. Such high-melting point waxes among those useful herein are disclosed in U.S. Pat. No. 4,049,792, to Elsnau, issued Sept. 20, 1977 (incorporated by reference herein).

Low melting point waxes include fatty acids, fatty alcohols, fatty acid esters, and fatty acid amides, having fatty chains of from about 8 to about 30 carbon atoms, preferably from about 12 to about 18 carbon atoms, and mixtures thereof. Preferred low melting point waxes include cetyl alcohol, palmitic acid, myristyl alcohol, stearyl alcohol, paraffin, cetyl stearate, cetyl palmitate, cetyl myristate, stearyl stearate, and mixtures thereof. Cetyl stearate, stearyl alcohol, cetyl alcohol, cetyl palmitate, cetyl myristate, stearyl stearate and mixtures thereof are particularly preferred. Also useful low melting point waxes include silicone waxes such as stearoxy dimethicone.

Paraffin wax is macrocrystalline, brittle, and is composed of from about 40% to about 90% paraffins and the remainder is $C_{18}$ to $C_{36}$ isoalkenes and cycloalkenes. Paraffin wax is derived from crude petroleum. Pure paraffin wax occurs in large plate-like hexagonal crystals which differentiates it from ozokerite and the so-called microcrystalline waxes. Paraffin crystals in needle form result from the presence of impurities. In its commercial form it contains less than 1% oil. Preferred paraffin waxes are characterized by a melting point of 120° F.–175° F. (50° C.–80° C.) and a penetration of 10–20 at 70° F. (25° C.) (as defined by ASTM D-1321) and a ratio of n-paraffins to iso-paraffins of from about 1:1 to about 20:1.

Microcrystalline waxes are relatively high melting point waxes and are distinguished from paraffin waxes by their smaller more flexible crystals and higher molecular weight. Generally they have a molecular weight in the range from about 400 to 1000. They are substantially water-insoluble but are able to be dispersed in aqueous micellar solutions of organic surfactants and/or in neat liquid organic surfactants, e.g., as colloidal or micellar solutions or as true solutions or emulsions. Particularly preferred microcrystalline waxes are characterized by a melting point of from about 150° F. to about 220° F. (about 66° C. to about 104° C.) and a penetration of from about 0.1 to about 10 at 77° F. (25° C.). Particularly preferred are the "hard" microcrystalline petrolatum waxes known as Be Square 195, Petrolite C-1035 and Petrolite C-700 all of which are sold by the Bareco Division, Petrolite Corporation, Tulsa, Okla.

Other very effective waxes include the "hard" microcrystalline Starwax 100, Be Square 185, Mekon Whiter, and Fortrex and the "plastic" microcrystallines Ultraflex, Victory and Be Square 175, all of which are also sold by the Bareco Division.

Wax type solidifying agents among those useful in the sticks of this invention are disclosed in the following, all of which are incorporated by reference herein in their entirety: U.S. Pat. No. 4,049,792, to Elsnau, issued Sept. 20, 1977; U.S. Pat. No. 4,151,272, to Geary et al., issued Apr. 24, 1975; U.S. Pat. No. 4,229,432, to Geria, issued Oct. 21, 1980; U.S. Pat. No. 4,280,994, to Turney, issued July 28, 1981; U.S. Pat. No. 4,126,679, to Davy et al., issued Nov. 21, 1978; and European Patent Application Publication Number 117,070, to May, published Aug. 29, 1984, "The Chemistry and Technology of Waxes", A. H. Warth, 2nd Edition, reprinted in 1960, Reinhold Publishing Corporation, pp 391–393 and 421; "The Petroleum Chemicals Industry", R. F. Goldstein and A. L. Waddeam, 3rd Edition (1967), E & F. N. Span Ltd., pp 33–40; "The Chemistry and Manufacture of Cosmetics", M. G. DeNavarre, 2nd edition (1970), Van Nostrand & Company, pp 354–376; and in "Encyclopedia of Chemical Technology:, Vol. 24, Kirk-Othmer, 3rd Edition (1979) pp 466–481.

The wax type solidifying agents typically comprise in total from about 5% to about 50%, preferably about 5% to about 35%, more preferably from about 10% to about 30%, and more preferably from about 15% to about 30% by weight of the compositions of the present invention.

Polyalphaolefins

The compositions of the present invention also essentially comprise one or more of a polyaplphaolefin of the formula:

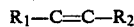

$$R_1-C=C-R_2$$

wherein $R_1$ and $R_2$ are independently from about $C_{20}$ to about $C_{70}$ alkyl, preferably about $C_{20}$ to about $C_{50}$, more preferably about $C_{30}$ to about $C_{50}$, and most preferably about $C_{20}$ to about $C_{40}$.

Useful polyalphaolefins have an average molecular weight of from about 300 to about 800 daltons, and a viscosity of from about 2 to about 10 centistokes at 100° C. The viscosity can be measured by means of a glass capillary viscometer as set forth in ASTM method D-88.

The polyalphaolefins preferably have a molecular weight ranging from about 445 to about 645 daltons and a viscosity ranging from about 4 to about 8 centistokes at 100° C.; and most preferably a molecular weight of from about 445 to about 555 daltons and a viscosity of from about 2 to about 4 centistokes at 100° C. The polyalphaolefins are available, for example, from the Emery Chemical Specialties Group as E-3004, E-3006. E-3008. and E-3010.

The polyalphaolefins typically comprise from about 5% to about 90%, preferably from about 10% to about 90% and most preferably from about 60% to about 80% of the total composition.

OPTIONAL COMPONENTS

Sunscreens

A wide variety of conventional sunscreening agents are suitable for use in the present invention. Segarin, et al., at Chapter VIII, pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, -phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol13,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisbenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane.

Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl12-cyano-3,3-diphenylacrylate, 2-ethylhexysalicylate, glyceryl p-aminobenzoate, 3,3,5-trimethylcyclohexysalicylate, methylanthranilate, p-dimethylaminobenzoic acid or aminobenzoate, 2-ethylhexyl p-dimethylamino- benzoate, 2-phenylbenzimidazole-5-sulfonic acid 2-(p-dimethylaminophenyl)-5-sulfonicbenzoxazoic acid and mixtures of these compounds, are particularly useful.

Preferred sunscreens useful in the compositions of the present invention are 2-ethylhexyl p-methoxycinnamate, butylmethoxydibenzoylmethane, 2-hydroxy-4-methoxybenzophenone, octyldimethyl p-aminobenzoic acid, 2,2'dihydroxy-4-methoxybenzophenone and ethyl hexyl salicylate and mixtures thereof.

A safe and photoprotectively effective amount of sunscreen may be used in the sunscreen compositions of the present invention. By "safe and photoprotectively" is meant an amount sufficient to provide photoprotection when the composition is applied not so much as to cause any side effects or skin reactions. Generally from about 1% to about 30%, preferably from about 2% to about 20%, of the composition may comprise a sunscreening agent. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the "lease exposure dose at a specified wavelength that will elicit a delayed erythema response". The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to a person with unprotected skin) before that person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. Commercially available sunscreening products have SPF values ranging from 2 to 50.

Also particularly useful in the present invention are sunscreens such as those disclosed in Sabatelli, U.S. patent application Ser. No. 054,085 (filed June 2, 1987) and Sabatelli et al., U.S. patent application Ser. No. 054,046 (filed June 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

These sunscreening agents provide higher efficacy, broader UV absorption, lower skin penetration and longer lasting efficacy relative to conventional sunscreens.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone, and N,N-di-(2-ethylhexyl)4-aminobenzoic acid ester of 4-(2-hydroxyethoxy)dibenzoylmethane and mixtures thereof.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference. The disclosed skin substantivity agent comprises the polymeric form of two monomers, ethylene and acrylic acid, to yield the following:

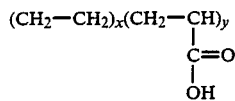

wherein the ratio of x:y is from about 1:24 to about 1:9, and wherein the weight average molecular weight of the molecule is from about 3500 to about 4500, preferably from about 4000 to about 4300. These copolymers are preferably included in an oil-in-water emulsion sunscreen composition comprising: (a) from about 1% to about 20% of the chelating agent plus an optional oil-soluble sunscreen; (b) from about 0.25% to about 3% of the ethylene-acrylic acid copolymer as described above; (c) from about 2% to about 10% of an emulsifier; and (d) from about 70% to about 90% of water, wherein the ratio of photoprotecting agents to the copolymer is from about 12:1 to about 15:1. Sunscreening agents which are particularly useful in combination with these copolymers are 2-ethylhexyl p-methoxycinnamate, butyl methoxydibenzoylmethane, 2-hydroxy-4-methoxybenzophenone, octyldimethyl p-aminobenzoic acid and mixtures thereof.

Antiperspirant Actives

Preferred antiperspirant actives useful herein include the following: Polyhydroxy complexes of basic aluminum salts as described in U.S. Pat. No. 3,420,932 to Jones et al., issued Jan. 7, 1969; U.S Pat. No. 3,359,169, to Slater et al., issued Dec. 19, 1967; U.S. Pat. No. 3,523,130 to Jones et al., issued Aug. 4, 1970; U.S. Pat. No. 3,507,896, to Jones et al., issued Apr. 21, 1970; U.S. Pat. No. 3,873,686, to Beekman, issued Mar. 25, 1975; U.S. Pat. No. 3,876,758 to Beekman, issued Apr. 8, 1975; and Britain Patent Specification No. 1,159,685 to Armour Pharmaceutical Co., published July 30, 1969 (all these disclosures being incorporated herein by reference in their entirety) and commercially-available as Rehydrol and Rehydrol II (supplied by Reheis Chemical Co.). Polyhydroxy derivatives of zinc and zirconium complexes of basic aluminum halides as described in U.S. Pat. No. 3,405,153, to Jones et al., issued Oct. 8, 1968; U.S. Pat. No. 3,555,146, to Jones et al., issued Jan. 12, 1971; Britain Patent Specification No. 1,159,686, to Jones et al., published July 30, 1969 (all these disclosures being incorporated herein by reference in their entirety). Zirconyl hydroxychloride salts, especially zirconium-aluminum-glycine complexes ("ZAG complexes"), as described in the following patent documents, all incorporated by reference herein in their entirety: Belgium Patent Specification No. 825,146, to Schmitz, issued Aug. 4, 1975; U.S. Pat. No. 2,814,585, to Daley, issued Nov. 26, 1957; U.S. Pat. No. 3,679,068, to Luedders et al., issued Feb. 12, 1974; U.S. Pat. No. 4,017,599, to Rubino, issued Apr. 12, 1977; U.S. Pat. No. 4,120,948, to Shelton, issued Oct. 17, 1978; and Britain Patent Specification No. 2,144,992, to Callaghan et al., published Mar. 20, 1985. Aluminum chlorhydroxide ("ACH") salts as described in the following documents, all incorporated by reference herein in their entirety: U.S. Pat. No. 3,887,692, to Gilman, issued June 3, 1975; U.S. Pat. No. 3,904,741, to Jones et al., issued Sept. 9, 1975; U.S. Pat. No. 4,359,456, to Gosling et al., issued Nov. 16, 1982; Britain Patent Specification No. 2,048,229, to Fitzgerald et al., published Dec. 10, 1980;

and Britain Patent Specification No. 1,347,950, to Shin et al., published Feb. 27, 1974.

Aluminum chlorhydroxide salts, zirconyl hydroxychloride salts, and mixtures thereof having improved molecular distributions are known, having been disclosed, for example, in the following documents, all incorporated by reference herein in their entirety: U.S. Pat. No. 4,359,456, to Gosling et al., issued Nov. 16, 1982; European Patent Application Publication No. 6,739, to Unilever Limited, published Jan. 9, 1980; European Patent Application Publication No. 183,171, to Armour Pharmaceutical Company, published June 4, 1986; British Patent Specification No. 2,048,229, to The Gillette Company, published Dec. 10, 1980; European Patent Application Publication No. 191,628, to Unilever PLC, published Aug. 20, 1986; and British Patent Specification No. 2,144,992, to The Gillette Company, published Mar. 20, 1985. Antiperspirant actives with enhanced efficacy due to improved molecular distribution are also described in European Patent Application Publication No. 7,191, to Unilever Limited, published Jan. 23, 1980, incorporated by reference herein in its entirety.

The improved molecular distribution is determined by the known analysis method called gel permeation chromatography. This analysis method is described, for example, in several of the above-incorporated patent specifications. It is preferred for purposes of the present invention that the antiperspirant active soluble in the polyhydric alcohol have enhanced efficacy due to improved molecular distribution having the ratio of peak 3 to peak 2 greater than about 0.1:1 as determined by gel permeation chromatography. This ratio, as is recognized by one skilled in the art, relates to the relative area under these two peaks as measured by the gel permeation chromatography analysis method.

The antiperspirant active typically comprise in total from about 1% to about 40%, preferably from about 10% to about 30%, and most preferably from about 10% to about 25%, of the compositions of the present invention.

Analgesic Actives

Preferred analgesic actives include methyl salicylate, turpentine oil, menthol, camphor, histamine dihydrochloride, methyl nicotinate, eucalyptus oil, triethanolamine salicylate, glycol salicylate and salicylamide and mixtures thereof. Suitable analgesic actives are fully described in "Handbook of Nonprescription Drugs", published by The American Pharmaceutical Association, seventh edition (1982) pp 514-523 which is incorporated by reference herein. The analgesic agent typically comprises from about 0.1% to about 40% by weight of the composition.

Emollients

The compositions of the present invention preferably comprise at least one emollient. Preferred emollients are volatile silicone oils, non-volatile emollients, and mixtures thereof. The compositions of the present invention more preferably comprise at least one volatile silicone oil which functions as a liquid emollient, or especially in a mixture of volatile silicone oils and non-volatile emollients. The term "volatile", as used herein, refers to those materials which have a measurable vapor pressure at ambient temperature.

Volatile silicone oils useful in the cosmetic stick compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the cosmetic stick compositions disclosed herein:

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries.* 91, pages 27-32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions in stick form also preferably contain one or more non-volatile emollients. Such materials include fatty acid and fatty alcohol esters, hydrocarbons, non-volatile silicone oils, and mixtures thereof. Emollients among those useful herein are described in 1 *Cosmetics, Science and Technology* 27-104 (M. Balsam and E. Sagarin, Ed.; 1972), and U.S. Pat. No. 4,202,879, to Shelton, issued May 13, 1980 (both incorporated by reference herein).

Non-volatile silicone oils useful as an emollient material include polyalkylsiloxanes, polyalklyarylsiloxanes, and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

Non-polar fatty acid and fatty alcohol esters useful herein as an emollient material include, for example, di-isopropyl adipate, isopropyl myristate, isopropyl palmitate, ethyl hexyl palmitate, isodecyl neopentanoate $C_{12}$–$C_{15}$ alcohol benzoate, diethyl hexyl maleate, PPG 14 butyl ether and PPG-2 myristyl ether propionate. Hydrocarbons such as isohexadecane (e.g., Permethyl 101A supplied by Presperse), petrolatum and USP light (e.g. Klearol®) or heavy (e.g. Kaydol®) are also useful as emollients.

The emollients typically comprise in total from about 10% to about 50%, preferably from about 15% to about 45%, and more preferably from about 20% to about 40% by weight of the compositions of the present invention.

Emulsifier

The cosmetic stick compositions of the present invention which contain an antiperspirant active and/or deodorant active also preferably comprise at least one emulsifier. Preferred is the use of a dimethicone copolyol, an organic emulsifier having an HLB value within the range of from about 1 to about 10, or a mixture of a dimethicone copolyol and an organic emulsifier.

The most preferred emulsifier for use in the compositions of the present invention is at least one silicone-containing material referred to herein as "dimethicone copolyol" which is one or more polyalkylene oxide modified dimethylpolysiloxanes. The dimethicone copolyols include the polyalkylene oxide modified dimethylpolysiloxanes of the following formulae:

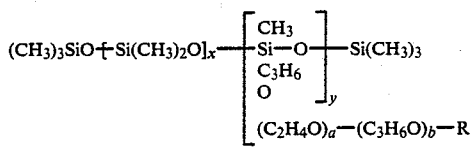

wherein R is hydrogen, an alkyl group having from about 1 to about 12 carbon atoms, an alkoxy group having from about 1 to about 6 carbon atoms, or a hydroxyl group; $R^1$ and $R^{11}$ are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Dimethicone copolyols among those useful herein are disclosed in the following patent documents, all incorporated by reference herein in their entirety: U.S. Pat. No. 4,122,029, to Gee et al., issued Oct. 24, 1978; U.S. Pat. No. 4,265,878, to Keil, issued May 5, 1981; and U.S. Pat. No. 4,421,769, to Dixon et al., issued Dec. 20, 1983. Commercially available dimethicone copolyols, useful herein, include Silwet Surface Active Copolymers (manufactured by the Union Carbide Corp.), Dow Corning Silicone Surfactants (manufactured by the Dow Corning Corp.); Silicone Copolymer F-754 (manufactured by SWS Silicones Corp.); and Rhodorsil 70646 Fluid (manufactured by Rohne Poulenc, Inc.). Dow Corning Q2-3225C Silicone Fluid is a preferred dimethicone copolyol.

Also preferred for use herein are organic emulsifiers, either alone or in combination with a dimethicone copolyol. If utilized alone, the organic emulsifier preferably has an HLB value within the range of from about 1 to about 10. The HLB (short for "Hydrophile-Lipophile Balance") value system is fully described, and values for various materials are provided, in the publication *The HLB System, A Time-Saving Guide to Emulsifier Selection* (published by ICI Americas Inc., Wilmington, Del.; 1984), the disclosures of which are incorporated herein by reference in their entirety. Examples of useful organic emulsifiers include sorbitan esters.

Also useful are ethoxylated fatty alcohol based emulsifiers, such as those sold by ICI Americas as Brij 78.

The emulsifier typically comprises in total from about 0.01% to about 15%, preferably from about 0.05% to about 10%, and most preferably from about 0.05% to about 5%, of the compositions of the present invention.

The compositions of the present invention may also contain optional components which modify the physical characteristics of the composition, or serve as "active" components when deposited on the skin. Additional active components include bacteriostats and fungistats. The particular non-active components that may be useful will typically depend upon the cosmetic properties that are desired. Such components include, for example, colorants and perfumes. Another optional component is a polar emollient such as, for example, propylene carbonate. While the compositions herein may also contain as an optional component some amount of a low boiling monohydric alcohol (e.g., ethanol; isopropanol), for reasons of cosmetic aesthetics it is preferred the compositions of the present invention contain less than about 10%, more preferably less, than about 5%, and most preferably about 0%, of a low boiling monohydric alcohol. Optional components useful herein are described in the following documents, all incorporated by reference herein: U.S. Pat. No. 4,049,792, to Elsnau, issued Sept. 20, 1977; Canadian Pat. No. 1,164,347, to Beckmeyer, et al., issued Mar. 27, 1984; European Patent Specification No. 117,070, to May, published Aug. 29, 1984; and Geria "Formulation of Stick Antiperspirants and Deodorants," 99 *Cosmetics & Toiletries* 55–60 (1984).

The specific essential and optional materials to be included in specific stick compositions of the present invention, and their levels, are selected in order to produce a stick of desired hardness so as to maintain dimensional stability while depositing a suitable amount of active material on the skin during normal use. Hardness of sticks can be determined in a variety of methods, including American Society for Testing Materials (ASTM) Method D-5. This method involves the use of a needle or polished cone of a particular weight and dimension, which is allowed to travel downward through the stick material for a predetermined period of time. The distance traveled by the needle or cone is a relative measure of the stick hardness. Utilizing Method D-5, with a penetration cone (Model H1310; sold by Humboldt Manufacturing Company) weighing 2.52 grams, and a Precision Model 14AN-8 Penetrometer (sold by GCA Corp.), the cosmetic sticks of the present invention preferably yield a penetration value of from about 3.0 to about 20.0 millimeters, more preferably from about 5.0 to about 15.0 millimeters, over a period of 5 seconds. These values represent an average penetration for sticks within a given production batch, since such penetration values may vary from stick to stick within the batch.

Another measure of the hardness of the preferred cosmetic sticks of the present invention is a break strength measurement. The break strength is determined using a Velmex Inc. Model B2509BJ (sold by Crown Tool & Supply Co.). In this instrument the force gauge is attached to a slide which allows the gauge to contact the test stick through a breaker bar at a speed of 3.3 inches per minute. The value recorded is the force gauge reading when the stick breaks. The cosmetic sticks of the present invention preferably have break strengths within the range of from about 3 to about 15 pounds.

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE I

An antiperspirant stick is prepared by combining the following components utilizing conventional mixing techniques.

| Components | % Weight |
| --- | --- |
| Stearyl Alcohol | 25.00 |
| Cyclomethicone D-5 | 20.00 |
| PAO 3004 | 20.00 |
| Aluminum Chlorhydrate | 25.00 |
| Castor Wax MP70 | 5.00 |
| PPG-14 Butyl Ether | 4.00 |
| Brij 78 | 1.00 |

Use of this stick by applying a thin layer to the underarm area of a human provides antiperspirant activity from a cosmetically-acceptable stick.

EXAMPLE II

An analgesic stick is prepared by combining the following components utilizing conventional mixing techniques.

| Components | % Weight |
| --- | --- |
| Methyl Salicylate | 20.00 |
| Menthol | 10.00 |
| PAO 3004 | 45.00 |
| Ozokerite | 25.00 |

Use of this stick by applying a thin layer to the forearm of a human provides analgesic efficacy from a cosmetically-acceptable stick.

EXAMPLE III

A moisturizing emollient stick is prepared by combining the following components utilizing conventional mixing techniques.

| Components | % Weight |
| --- | --- |
| Ozokerite | 20.00 |
| PAO 3004 | 58.95 |
| Petrolatum | 20.00 |
| Tocophepyl Acetate | 1.00 |
| Propyl Paraben | 0.05 |

Use of this stick by applying a thin layer to the face of a human provides moisturizing from a cosmetically-acceptable stick.

EXAMPLE V

A sunscreen stick is prepared by combining the following components utilizing conventional mixing techniques.

| Components | % Weight |
| --- | --- |
| Stearyl Alcohol | 30.00 |
| Cyclomethicone | 20.00 |
| PA 3004 | 34.50 |
| Octyl Methoxycinnamate | 7.50 |
| Benzophenone-3 | 3.00 |
| Octyl Salicylate | 5.00 |

This stick is useful for topical application, for example to the face, to inhibit damage caused by acute or chronic UV exposure. Use of an amount of stick sufficient to deposit about 0.5 to about 3 mg/cm$^2$ of the sunscreen actives (octyl methoxy cinnamate, benzophenone-3, octyl salicylate) immediately prior to UV exposure is appropriate.

Substantially similar results are obtained if the sunscreen component (octyl methoxycinnamate, benzophenone-3, octyl salicylate) is replaced, in whole or in part with benzophenone-8, octyl dimethyl PABA, 2-ethylhexyl p-methoxycinnamate, butylmethoxy-dibenzoylmethane, 2-hyxroxy-4-methoxybenzophenone, and mixtures thereof.

EXAMPLES V-VIII

Sunscreen Stick Compositions

| | % w/w | | | |
| --- | --- | --- | --- | --- |
| Ingredients | Ex. V | Ex. VI | Ex. VII | Ex. VIII |
| Ozokerite Wax | 25.00 | 25.00 | 23.00 | 23.00 |
| Klearol ® Mineral Oil | 14.75 | — | — | — |
| Petrolatum Perfecta | 10.00 | 10.00 | — | — |
| Octyl Dimethyl PABA | 8.00 | 8.00 | 8.00 | 8.00 |
| Octyl Methoxy Cinnamate | 3.00 | 3.00 | 3.00 | 3.00 |
| Benzophenone-3 | 3.00 | 3.00 | 3.00 | 3.00 |
| Propylparaben | 0.10 | 0.10 | 0.10 | 0.10 |
| Vitamin E Acetate | 0.50 | 0.50 | 0.50 | 0.50 |
| Silicone SWS F755 | 0.50 | 0.50 | 0.50 | 0.50 |
| Frag. 49.073/T. Firmenich | 0.15 | 0.15 | 0.15 | 0.15 |
| Permethyl 101A | — | 24.75 | — | — |
| PAO 3004 | 25.00 | 25.00 | 59.75 | 49.75 |
| Ft-150 Wax | — | — | 2.00 | — |
| Syncrowax HGL-C | — | — | — | 10.00 |
| AC Polymer 400A | — | — | — | 2.00 |

EXAMPLES IX-XI

Sunscreen Stick Compositions

| | % w/w | | |
| --- | --- | --- | --- |
| Ingredients | Ex. IX | Ex. X | Ex. XI |
| Ozokerite Wax | 23.00 | 12.50 | 12.50 |
| PAO 3004 | 49.75 | 59.75 | 35.25 |
| Petrolatum Perfecta | 10.00 | — | 20.00 |
| Octyl Dimethyl PABA | 8.00 | 8.00 | — |
| Octyl Methoxy Cinnamate | 3.00 | 3.00 | 7.50 |
| Benzophenone-3 | 3.00 | 3.00 | 6.00 |
| Propylparaben | 0.10 | 0.10 | 0.10 |
| Vitamin E Acetate | 0.50 | 0.50 | 0.50 |
| Silicone SWS F755 | 0.50 | 0.50 | — |
| Fragrance | 0.15 | 0.15 | 0.15 |
| AC Polymer 400A | — | 12.50 | — |
| Candelilla | — | — | 12.50 |
| Octyl Salicylate | — | — | 5.00 |

-continued

| Ingredients | % w/w | | |
|---|---|---|---|
| | Ex. IX | Ex. X | Ex. XI |
| Benzophenone-8 | — | — | 0.50 |

What is claimed is:

1. A cosmetic stick composition comprising:
   (a) from about 10% to about 50% of a wax-type solidifying agent selected from the group consisting of beeswax, spermaceti, carnauba, baysberry, candelilla, montan, ozokerite, ceresin, paraffin, hydrogenated castor oil, Fisher-Tropsch waxes, microcrystalline waxes, ethylene glycol diesters, triglyceride waxes and ethylene/vinyl acetate copolymers, and mixtures thereof;
   (b) from about 5% to about 90% of one or more of a polyalphaolefin of the formula:

$$R_1-C=C-R_2$$

wherein $R_1$ and $R_2$ are independently $C_{20}$ to $C_{70}$ alkyl and wherein said polyalphaolefin has an average molecular weight of from about 300 to about 800 daltons and a viscosity of from about 2 to about 10 centistokes at 100° C.;
   (c) from about 1% to about 40% of an active component selected from the group consisting of sunscreens, analgesics, moisturizers, antiperspirants and deodorants and mixtures thereof;
   (d) from about 10% to about 50% of an emollient; and
   (e) from about 0.01 to about 15% of an emulsifier.

2. A cosmetic stick composition according to claim 1 wherein said wax-type solidifying agent is present at a level of from about 5% to about 35%.

3. A cosmetic stick composition according to claim 2 wherein said polyalphaolefin is present at a level of from about 10% to about 80% and wherein $R_1$ and $R_2$ are indpendently from about $C_{20}$ to about $C_{50}$.

4. A cosmetic stick composition according to claim 3 wherein said polyalphaolefin has an average molecular weight of from about 445 to about 645 daltons and a viscosity of from about 4 to about 8 centistokes at 100° C.

5. A cosmetic stick composition according to claim 4 wherein said active composition is a sunscreen.

6. A cosmetic stick composition according to claim 5 wherein said sunscreen active is selected from the group consisting of 2-ethylhexyl p-methoxycinnamate, butyl-methoxydibenzoylmethane, 2-hydroxy-4-methoxybenzophenone, 2,2'dihydroxy-4-methoxybenzophenone and ethyl hexyl salicylate, octyldimethyl p-aminobenzoic acid, the 4-N,N-(2-ethylhexyl)methylaminobenzoic acid ester of 2,4-dihydroxybenzophenone, the N,N-di-(ethylhexyl)-4-aminobenzoic acid ester of 4-hydroxydibenzoylmethane, the 4-N,N-(2-ethylhexyl)methylaminobenzoic acid ester of 4-hydroxydibenzoylmethane, the 4-N,N-(2-ethylhexylmethylaminobenzoic acid ester of 2-hydroxy-4-(2-hydroxyethoxy) benzophenone, the 4-N-N-(2-ethylhexyl)methylaminobenzoic acid ester of (4-(2-hydroxyethoxy) dibenzoylmethane, the N-N-di-(2-ethylhexyl)-4-aminobenzoic acid ester of 2-hydroxy-4-(2-hydroxyethoxy)benzophenone, or the N,N-di-(2-ethylhexyl)-4aminobenzoic acid ester of 4-(2-hydroxyethoxy)dibenzoylmethane and mixtures thereof.

7. A cosmetic stick composition according to claim 6 wherein said sunscreen active is selected from the group consisting of 2-ethylhexyl p-methoxycinnamate, butyl-methoxydibenzoylmethane, 2-hydroxy 4-methoxybenzophenone, octyldimethy p-aminobenzoic acid and mixtures thereof.

8. A cosmetic stick composition according to claim 4 wherein said emollient is selected from the group consisting of petrolatum, lanolin, tocopheryl acetate, USP light mineral oil, USP heavy mineral oil, isohexadecane, isodecyl neopentanoate, and mixtures thereof.

9. A cosmetic stick composition according to claim 4 wherein said active is selected from the group consisting of aluminum chlorhydroxide aluminum hydroxybromide, mixtures of aluminum chlorhydroxide and aluminum chloride and complexes formed from zirconium hydroxychloride, aluminum chlorhydroxide and glycine.

10. A cosmetic stick composition according to claim 4 wherein said active is an analgesic active selected from the group consisting of methyl salicylate, turpentine oil, menthol, camphor, histamine dihydrochloride, methyl nicotinate, eucalyptus oil, triethanolmine salicylate glycol salicylate and salicylamide and mixtures thereof.

* * * * *